(12) United States Patent
Frevel

(10) Patent No.: US 7,781,420 B2
(45) Date of Patent: Aug. 24, 2010

(54) USE OF CLODRONIC ACID FOR TREATMENT PODOTROCHLOSIS

(75) Inventor: Michael Frevel, Bedburg (DE)

(73) Assignee: Omnimedic GbR, Dortmund (DE)

( * ) Notice: Subject to any disclaimer, the term of this patent is extended or adjusted under 35 U.S.C. 154(b) by 0 days.

(21) Appl. No.: 12/084,587

(22) PCT Filed: Nov. 9, 2006

(86) PCT No.: PCT/EP2006/010753

§ 371 (c)(1),
(2), (4) Date: May 23, 2008

(87) PCT Pub. No.: WO2007/054309

PCT Pub. Date: May 18, 2007

(65) Prior Publication Data

US 2009/0253657 A1    Oct. 8, 2009

(30) Foreign Application Priority Data

Nov. 9, 2005    (DE) .................. 10 2005 053 512

(51) Int. Cl.
*A61K 31/66* (2006.01)
(52) U.S. Cl. ..................................... 514/108
(58) Field of Classification Search .................. 514/108
See application file for complete search history.

(56) References Cited

U.S. PATENT DOCUMENTS

| 6,280,741 | B1 * | 8/2001 | Jessup ..................... 424/256.1 |
| 2003/0031731 | A1 * | 2/2003 | Bar ........................... 424/680 |
| 2004/0019269 | A1 * | 1/2004 | Schaefer et al. ............. 600/407 |
| 2004/0038944 | A1 * | 2/2004 | Thompson ................... 514/80 |
| 2005/0153359 | A1 * | 7/2005 | Schaefer et al. .............. 435/7.1 |

* cited by examiner

*Primary Examiner*—Raymond J Henley, III
(74) *Attorney, Agent, or Firm*—The Nath Law Group; Joshua B. Goldberg; Tanya E. Harkins

(57) ABSTRACT

The invention describes the use of clodronic acid, its addition salts or esters as active ingredient for the preparation of a pharmaceutical for treating podotrochlosis with associated osteoporosis in horses.

9 Claims, No Drawings

USE OF CLODRONIC ACID FOR TREATMENT PODOTROCHLOSIS

FIELD OF THE INVENTION

The present invention relates to the use of clodronic acid, its addition salts or esters, hydrates or salts of hydrates for the treatment of podotrochlosis with associated osteoporosis in horses and to the use of clodronic acid, its addition salts or esters as active ingredient for the preparation of a pharmaceutical for treating podotrochlosis with associated osteoporosis in horses.

BACKGROUND OF THE INVENTION

In equine medicine, the disease "podotrochlitis" or "podotrochlosis", commonly also referred to as "navicular syndrome", is a widespread disease in the distal section of the horse's forelimb. The traditional form of the disease has been described as a chronic, progressive and degenerative disease with involvement of the navicular bone, the navicular bursa and the flexor tendon.

In horses, genetic predisposition, inadequate keeping, poor or irregular training, severe strain and age frequently result in an atrophy of the navicular bone, which leads to a demineralization of the bone. The subchondral bone will then, as a result of the unphysiological pressure conditions which act on the bone, undergo osteoporotic change.

In the early stages of the disease, the subchondral bone comprises a large number of widened vascular ducts which are filled with granulation tissue and surrounded by osteoclasts and osteoblasts. During the pathogenesis, osteoclastic changes develop which approach the compact tissue of the tendons' gliding surface, whereby the latter becomes thin, and microfractures of the palmar compact tissue may result. This primarily gives rise to osteoclasis of the subchondral bone.

When these disease symptoms occur, a periodic chronic lameness results, and this leads in most cases to the horse's long-term unusability.

PRIOR ART

Since podotrochlosis is one of the main causes of lameness in horses, and in the light of the frequency of the above-described symptoms, a large number of therapeutic attempts have been made in the past, both in the pharmaceutical and in the surgical and natural healing sector.

EP 0 854 724 B1 describes the use of certain bisphosphonates, including clodronic acid, for treating navicular syndrome in horses. As regards the cause of the disease, two theories are being put forward, firstly poor circulation within the leg and secondly changes in the biomechanical properties of the limb in question. The pharmaceutical may be given enterally, parenterally or transdermally, preferably intravenously.

However, the therapeutic attempts known to date have been without noticeable success. The consequence for the animal is permanent pain combined with restricted movement and the unusability of the horse for leisure or competitive equestrianism, combined with a substantial emotional and financial loss for the owner.

It has recently emerged that another substance from the bisphosphonate class, namely tiludronate, has a healing effect on podotrochlosis. However, this effect is frequently associated with substantial side effects such as colic, and, furthermore, the prescribed administration of the active ingredient by infusion and intravenous injection entails considerable disadvantages for the animal and the treating veterinarian.

PROBLEM OF THE INVENTION

The invention is therefore based on the problem of providing an effective pharmaceutical for treating podotrochlosis with associated osteoporosis in horses.

SUMMARY OF THE INVENTION

According to the invention, it has now been shown that chlodronic acid can be employed in an efficient manner for treating podotrochlosis in horses, provided that the pharmaceutical is administered as per the regimen defined in claim 1. In particular, osteoporotic states in the navicular bone area of horses can successfully be treated in accordance with the invention.

The invention therefore relates to the use of clodronic acid, its addition salts or esters, hydrates or salts of hydrates as active ingredient for the preparation of a pharmaceutical in the form of an injectable solution or suspension for the treatment of podotrochlosis with associated osteoporosis in horses, the treatment being carried out by two to five intramuscular injections of the pharmaceutical within the period of up to several days.

Preferred, or especially expedient, embodiments of the inventive subject are detailed in the dependent claims.

DETAILED DESCRIPTION OF THE INVENTION

Clodronic acid is the international nonproprietary name for (dichloromethylene)bis(phosphonic acid). The disodium salt of clodronic acid is employed in human medicine in diseases involving hypercalcemia, in particular in hypercalcemia as the result of bone metastases of solid tumors or osteolysis, induced by malignant tumors, without bone metastases. A pharmaceutical comprising clodronic acid, disodium salt 4 $H_2O$ is commercially available for example under the name Bonefos®.

In accordance with the invention, it has now been shown that outstanding therapeutic successes can be achieved with clodronic acid in the treatment of podotrochlosis with associated osteoporosis in horses, so that the majority of the treated horses can be used again regularly as riding horses or sport horses.

In accordance with the invention, suitable addition salts of chlodronic acid are in particular the alkali metal salts, with the disodium salt, in particular the disodium salt $4H_2O$, being most suitable and preferred.

The pharmaceutical employed in accordance with the invention in the form of an injectable solution or suspension may comprise conventional adjuvants and excipients such as, for example, binders, buffers, glidants, diluents and colorants. The injectable solution or suspension is prepared in a manner known per se.

To achieve the desired therapeutic success or else prophylactic success, a dosage regimen in which the pharmaceutical is administered by two to five intramuscular injections within a period of up to several days, such as approximately 3 consecutive days, but preferably within one day, must be adhered to. Here, the administration of the pharmaceutical may be effected in a dosage of, per injection, 0.125-2.5 mg, preferably 0.25-1 mg, particularly preferably approximately 0.6 mg of active ingredient/kg body weight. For a horse with a weight of 500 kg, a total dose of 250-2500 mg, preferably 400-1500 mg, especially preferably approximately 800 to 1000 mg of active ingredient, distributed over 2 to 5 injections, preferably 3 injections, is aimed at. With a horse with a weight of 500 kg, it is therefore especially preferable to administer 900 mg of active ingredient, divided over 3 injections of 300 mg each, within one day. The pharmaceutical is injected intramuscularly, preferably into the neck, chest and gluteal muscles of the horse. In the case of 3 injections, it is preferred to administer two injections into the neck muscles (on the left and right side), especially preferably approximately one hand's width under the crest and approximately one hand's width above the scapula, and one injection into the breast muscles. The 2 to 5 injections are expediently given directly one after the other.

After approximately 14 days, a pronounced improvement of the clinical symptoms is observed in nearly all horses. After approximately 4-6 weeks, the clinical picture has stabilized and established such that the therapeutic success can be defined. After approximately 10 to 14 months, the clinical symptoms will, as a rule, deteriorate. The treatment may then be repeated once or more than once, with equally good success. In this manner, the treated horses can be kept free from lameness over several years.

To date, at least 350 horses who suffer from podotrochlosis and which have been pretreated with conventional therapies without success have received successful therapy with the pharmaceutical described in accordance with the invention, and without suffering side effects. Many of the horses treated thus have been free from lameness for several years with the regular use of this pharmaceutical. For example, the therapeutic success in a gelding who had suffered from podotrochlosis and who had not been able to be ridden, let alone used as a sports horses for about 3 years was so good after employing the pharmaceutical described in accordance with the invention that the gelding could afterwards be used intensively and successfully for 6 years as a showjumper.

I claim:

1. A method for treating podotrochlosis with associated osteoporosis in horses comprising:
    administering to the horses a pharmaceutical composition in the form of an injectable solution or suspension comprising as an active ingredients an effective amount of clodronic acid, addition salts or esters thereof, or hydrates or salts of hydrates thereof,
    wherein the administration is carried out by two to five intramuscular injections of the pharmaceutical composition within a period of up to approximately 3 consecutive days.

2. The method as claimed in claim 1, wherein the addition salts of clodronic acid are alkali metal salts.

3. The method as claimed in claim 2, wherein the alkali metal salts is disodium salt of clodronic acid.

4. The method as claimed in claim 1, wherein the pharmaceutical composition further comprises adjuvants and/or excipients.

5. The method as claimed in claim 1, wherein the administration is carried out by two to five intramuscular injections of the pharmaceutical composition within one day.

6. The method as claimed in claim 1, wherein the administration is repeated once or more than once after 10-14 months have elapsed.

7. The method as claimed in claim 1, wherein the pharmaceutical composition is administered at a dosage, per injection, of 0.125-2.5 mg active ingredient/kg body weight.

8. The method as claimed in claim 7, wherein the pharmaceutical composition is administered at a dosage, per injection, of 0.25-1 mg active ingredient/kg body weight.

9. The method as claimed in claim 8, the pharmaceutical composition is administered at a dosage, per injection, of approximately 0.6 mg of active ingredient/kg body weight.

* * * * *